United States Patent
Cecchi et al.

[19]

[11] Patent Number: 6,165,165
[45] Date of Patent: Dec. 26, 2000

[54] EMBRYO-IMPLANTING CATHETER ASSEMBLY AND METHOD FOR MAKING THE SAME

[75] Inventors: Michael D. Cecchi, Madison, Conn.; Jacques Cohen, Mountain Lakes, N.J.

[73] Assignee: Genx International, Inc., Madison, Conn.

[21] Appl. No.: 09/393,006

[22] Filed: Sep. 9, 1999

Related U.S. Application Data

[60] Provisional application No. 60/102,841, Oct. 2, 1998.

[51] Int. Cl.$^7$ .................................................. A61M 25/00
[52] U.S. Cl. ........................ 604/523; 604/264; 264/209.1
[58] Field of Search .................................... 604/523, 264, 604/525, 528, 530; 264/209.1, 171.1

[56] References Cited

U.S. PATENT DOCUMENTS

| | | | |
|---|---|---|---|
| 4,863,423 | 9/1989 | Wallace | 604/48 |
| 5,254,107 | 10/1993 | Soltesz | 604/282 |
| 5,403,292 | 4/1995 | Ju | 604/282 |
| 5,509,408 | 4/1996 | Kurtis | 128/207.14 |
| 5,542,937 | 8/1996 | Chee et al. | 604/280 |
| 5,599,325 | 2/1997 | Ju et al. | 604/282 |
| 5,622,665 | 4/1997 | Wang et al. | 264/150 |
| 5,725,513 | 3/1998 | Ju et al. | 604/280 |
| 5,772,641 | 6/1998 | Wilson | 604/280 |
| 6,016,811 | 1/2000 | Knopp et al. | 128/898 |

FOREIGN PATENT DOCUMENTS

| | | | |
|---|---|---|---|
| 0 528 181 A1 | 2/1993 | European Pat. Off. | B29C 47/58 |
| 0 618 059 A1 | 10/1994 | European Pat. Off. | B29C 47/04 |

*Primary Examiner*—Sharon Kennedy
*Assistant Examiner*—Kevin C. Sirmons
*Attorney, Agent, or Firm*—William W. Jones

[57] ABSTRACT

An embryo implant catheter assembly includes an outer guide cannula and an inner catheter which is slidably disposed in the guide cannula. The inner catheter is operable to engage an embryo to be implanted in a female's uterus. The embryo is disposed in a distal end of the catheter, which distal end is inserted into the uterus during the implant procedure. The catheter has a varying stiffness from the distal end to an opposite proximal end, the distal end being softer and the proximal end being more rigid. The result is a catheter that is non-abrasive at its distal end, and resistant to wobble at its proximal end. The catheter is produced by extruding mixtures of resins which have different durometers, and varying the percentage of the resins in the mixture along the length of the catheter.

13 Claims, 3 Drawing Sheets

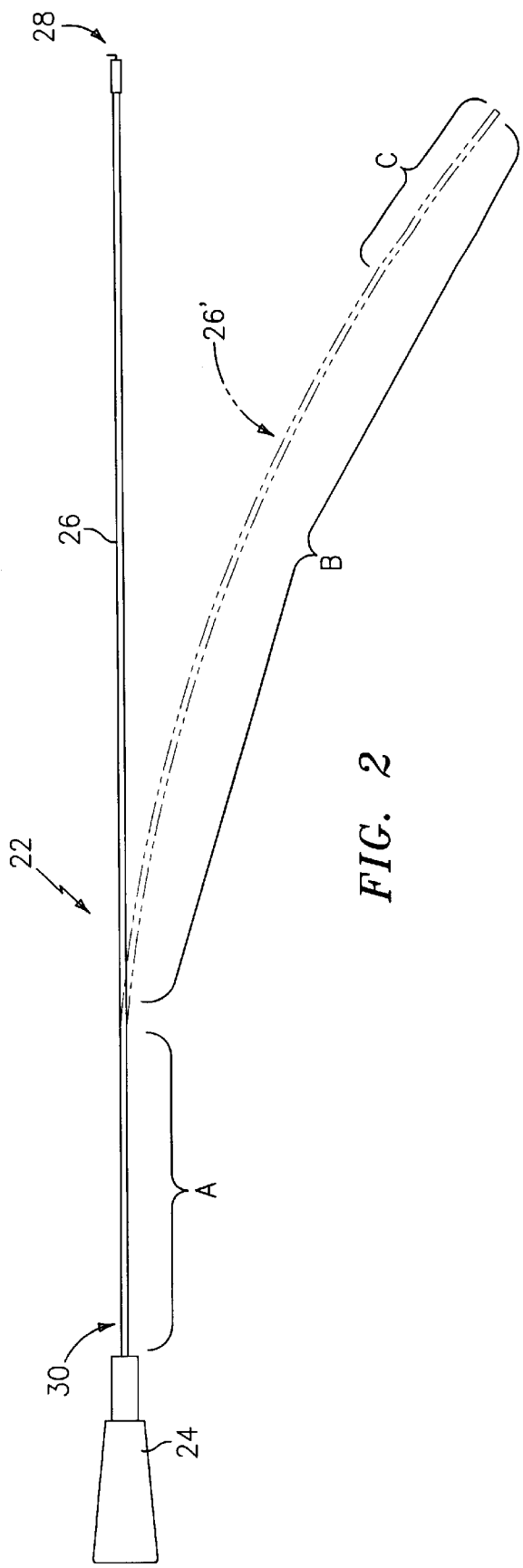
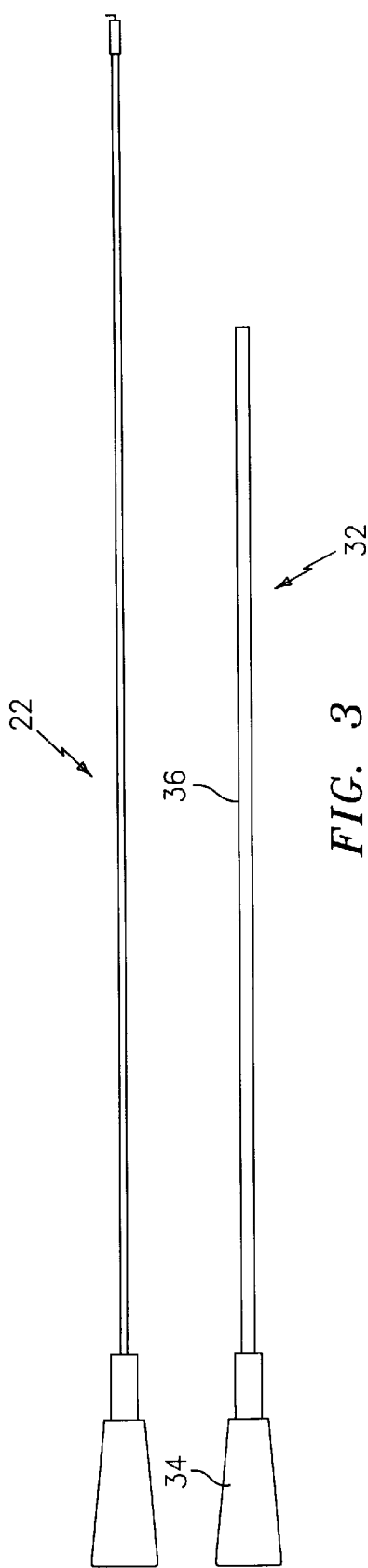
FIG. 2
FIG. 3

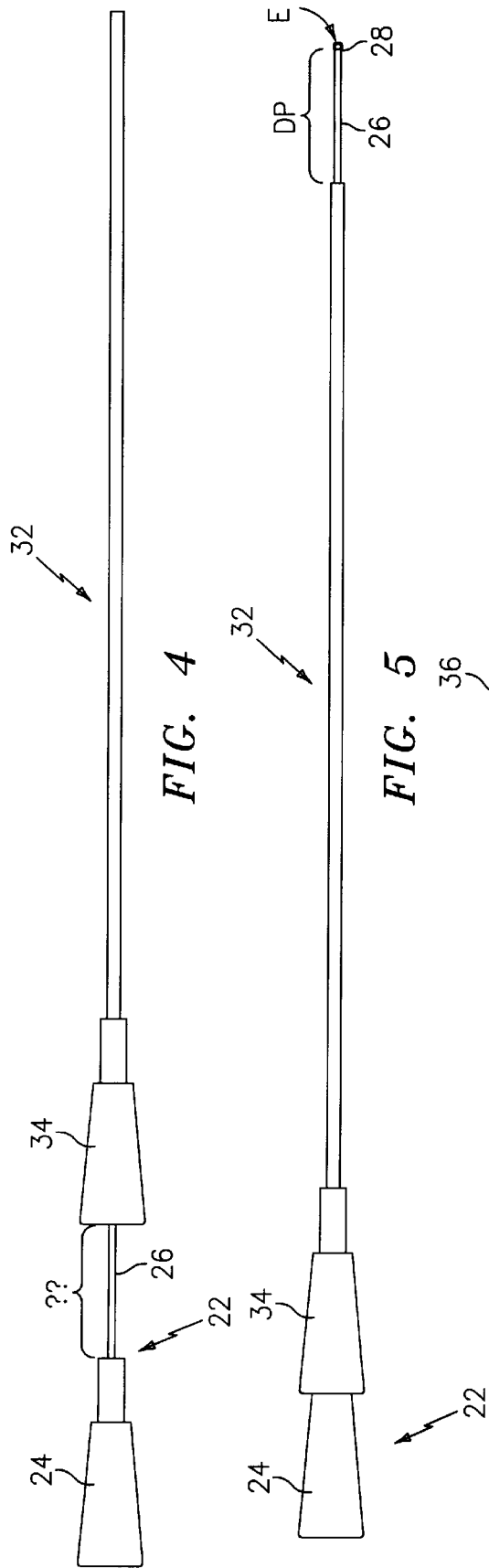
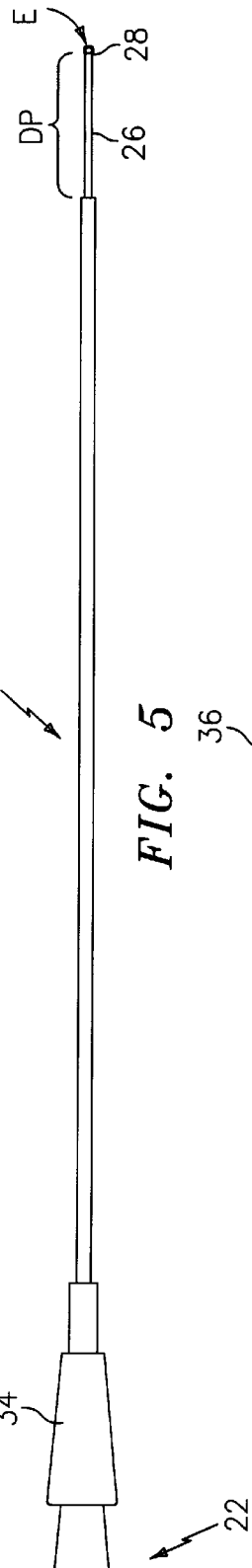
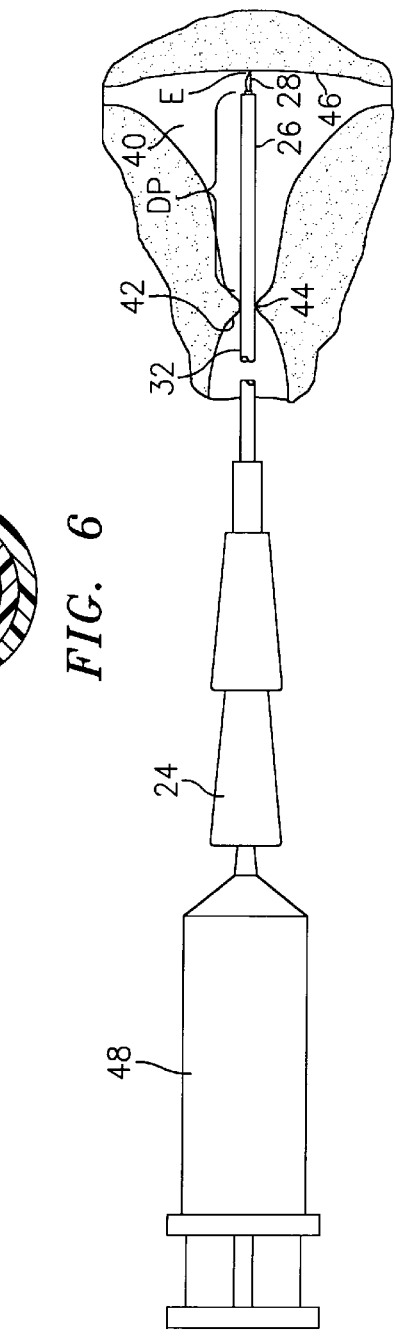
FIG. 4
FIG. 5
FIG. 6
FIG. 7

EMBRYO-IMPLANTING CATHETER ASSEMBLY AND METHOD FOR MAKING THE SAME

This application claims the benefit of U.S. Provisional Patent Application Ser. No. 60/102,841, filed Oct. 2, 1998.

TECHNICAL FIELD

This invention relates to a catheter assembly which includes an outer guide cannula and an inner catheter which is slidably disposed in a bore in the guide cannula. The catheter assembly is particularly useful for safely depositing an embryo on the uterine wall of a female seeking to conceive. The catheter includes a soft distal end which carries the embryo, and a more rigid proximal end which allows controlled advancement of the catheter through the guide cannula once the guide cannula has penetrated the uterine cervix. This invention also relates to a method of making the inner catheter.

BACKGROUND ART

Catheters for use in penetrating various passages in the human body for various procedures are well known in the prior art. Uses for such catheters include: penetrating cardiac blood vessels; penetrating cerebral blood vessels; and penetrating the uterus in embryo implant procedures, for example. Catheters used in the aforesaid procedures all include a distal end which penetrates the body passages, and a proximal end which remains outside of the body and is used to manually "steer" the distal end of the catheter through the body passages. The aforesaid catheters are typically inserted into the body through the bore of a proximal catheter guide cannula which penetrates the body. Once the guide cannula penetrates the body passage in question, the catheter is advanced into the body passage through the guide cannula.

In order to avoid damaging delicate body tissues, the distal tip of the catheter should be formed from a soft material. U.S. Pat. No. 4,531,943, Van Tassel et al; U.S. Pat. No. 4,863,442, DeMello et al; U.S. Pat. No. 4,886,506, Lovgren et al; U.S. Pat. No. 5,045,072, Castillo et al; U.S. Pat. No. 5,221,270, Parker; U.S. Pat. No. 5,234,416, Macaulay et al; U.S. Pat. No. 5,571,073, Castillo; U.S. Pat. No. 5,769,830, Parker; and U.S. Pat. No. 5,792,124, Horrigan et al all describe catheters that are provided with soft distal ends so as to avoid tissue damage when inserted into the body. The prior art also recognizes the fact that while the distal end of the catheter should be soft, more proximal portions of the catheter should preferably be more rigid in order to facilitate pushing of the catheter into the body through the guide cannula. The aforesaid patents all disclose catheter structures which are provided with a soft distal tip and a more rigid proximal portion. In each case, the softer distal tip portion of the catheter is a separate element which is attached to the stiffer proximal portion, and the stiffer proximal portion is typically reinforced with a stiffener, such as a braid or the like. The prior art catheters described in the above-identified patents are thus complex structures and require assembly.

Another approach to the production of a soft distal tip catheter which has been proposed is a catheter wherein both the distal and proximal portions of the catheter are formed from the same soft material. This type of catheter avoids the complexity of the aforesaid patented catheters and also avoids the need to assemble the distal and proximal catheter portions, however, this approach produces a catheter that is difficult to steer through the guide cannula due to the tendency of the proximal portion of the catheter to flex or wobble when the physician attempts to push the catheter into the subject's body through the guide cannula. This problem requires a second attendant, typically a nurse, to try to manually prevent the catheter from flexing as the physician advances the catheter into the body.

The aforesaid problem of catheter flexure, or wobble, is particularly troublesome in the field of implanting of embryo into a female's womb. This problem may be the result of the cervical constriction which is encountered by a physician during the implant procedure. When an embryo is implanted in a female's uterus, the guide cannula will be advanced into the os of the cervix. During insertion of the guide cannula, the embryo implant catheter will be retracted completely inside of the guide cannula so as to protect the embryo. Once the guide cannula is in position in the cervix os, the inner catheter, the distal tip of which holds the embryo to be implanted, is then advanced through the guide cannula and through the cervix and into the uterus. Thus, a catheter which is formed solely from a soft material will be difficult to insert into the womb due to the cervical constriction adjacent to the cervical os.

It would be highly desirable to provide a catheter, particularly an embryo implant catheter, which has a soft distal tip and also has a stiffer proximal portion, which catheter does not require assembly, and is formed from a homogeneous material.

DISCLOSURE OF THE INVENTION

This invention relates to an improved catheter assembly which is particularly useful in performing embryo implants in a female's uterus. This invention also relates to a method for forming the improved catheter assembly, and to an improved guide cannula for use in conjunction with the catheter assembly. The catheter assembly of this invention includes a soft distal tip for supporting the embryo to be implanted in the womb, and a more rigid proximal portion which facilitates insertion of the distal tip and embryo into the womb through the cervix. The catheter assembly includes a hollow rigid proximal hub which is grasped by the physician during the implant procedure, and a hollow tubular member which has its proximal end attached to the hub, and has a distal end which supports the embryo.

The distal end of the tubular member is soft, typically having a durometer of about 80 Shore A, and the proximal end of the tubular member is stiffer, typically have a durometer in the range of about 55 to about 75 Shore D. The tubular member is formed from an extruded resin such as PVC or polyurethane. The proximal end of the tubular member resin is formed from a stiffer durometer grade of the resin, and the distal end of the tubular member is formed from a softer durometer grade of the resin. The transition from the softer durometer grade to the stiffer durometer grade of the resin can be accomplished during extrusion of the tubular member either linearly or step-wise.

The extruder assembly will preferably include first and second resin hoppers, a first of which will contain the stiffer durometer grade resin, and a second of which will contain the softer durometer grade resin. The hoppers will be connected to a mixing chamber via feed valves so that the resins contained in the hoppers can be selectively mixed in the mixing chamber, and the mixing chamber will be connected to an extrusion head. At commencement of the extrusion process, only resin from one hopper, either the first or second, will be fed into the mixing chamber. After a controlled time period, resin from the other hopper will be fed into the mixing chamber along with resin from the first hopper so that a mixture of the two resins will be produced in the mixing chamber. At the time that the extrusion process is completed, only resin from the other hopper will be fed into the mixing chamber. If a gradual change from the soft to the hard resin is desired, the mixture of the two resins will be altered gradually. If a step-wise change from the soft to the hard resin is desired, the mixture of the two resins will be altered at predetermined time intervals during the extrusion step. Preferably, the soft distal end of the catheter tube will be at least one centimeter long, and thereafter the catheter tube will become stiffer. Continuous extrusion of the tubular portion of the catheter assembly can proceed from stiff end to soft end, and then from soft end to stiff end, and so on. An extrusion process controller can be employed to control the mixing of the resins in the mixing chamber.

The guide cannula is preferably formed from co-extruded concentric selected resins, the inner of which resin is a low coefficient of friction, or "slippery" resin, such as nylon, for example; and the outer of which is a resin which has a higher coefficient of friction, and possesses memory so that the guide cannula can be easily grasped, and can be bent, and will retain its bent configuration.

It is therefore an object of this invention to provide an improved embryo implant catheter which includes a soft distal end portion and a stiffer proximal end portion which facilitates insertion of the catheter from a guide cannula through the cervix of an embryo implant candidate.

It is another object of this invention to provide an embryo implant catheter of the character described wherein the durometer of the soft distal tip of the catheter can be varied.

It is a further object of this invention to provide an embryo implant catheter of the character described wherein the tubular embryo transfer portion of the catheter is formed from a homogeneously extruded tubular member.

It is another object of this invention to provide an embryo implant catheter of the character described wherein the tubular embryo transfer portion of the catheter Is formed from an extruded resin mixture having different durometers as measured from the distal end of the embryo transfer portion to the proximal end of the embryo transfer portion of the catheter.

It is an additional object of this invention to provide a method for forming an embryo implant catheter of the character described.

It is yet another object of this invention to provide an embryo implant catheter assembly which includes a guide cannula having an inner component formed from a low friction resin material, and an outer jacket which is formed from a higher friction resin material having deflection memory.

BRIEF DESCRIPTION OF THE DRAWINGS

These and other objects and advantages of the invention will become more readily apparent from the following detailed description of several embodiments of the invention when taken in conjunction with the accompanying drawings in which:

FIG. 2 is a side elevational view of a catheter assembly formed in accordance with this invention;

FIG. 3 is an exploded view of the catheter assembly and guide cannula assembly formed in accordance with this invention;

FIG. 4 is a side elevational view of the catheter assembly and guide cannula assembly with the catheter assembly partially retracted into the guide cannula;

FIG. 5 is a side elevational view of the catheter assembly fully inserted into the guide cannula assembly;

FIG. 6 is a cross-sectional view of the guide cannula showing the inner and outer components thereof; and FIG. 7 is a schematic view showing how the catheter and guide cannula assembly is used to implant an embryo in the womb of a female being treated with the assembly.

DETAILED DESCRIPTION OF SPECIFIC EMBODIMENTS OF THE INVENTION

Figure 1:
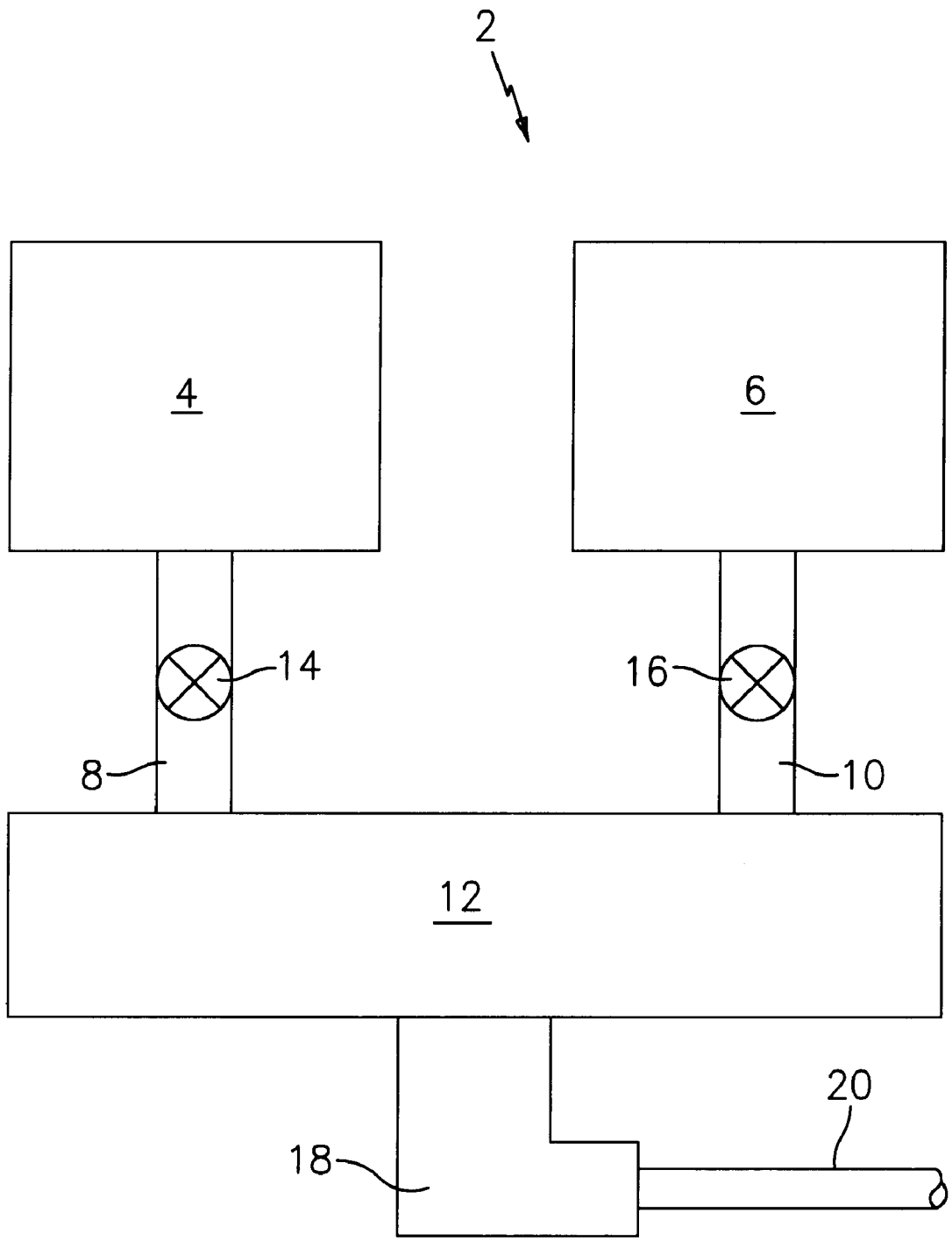
FIG. 1 is a schematic view of a resin extrusion assembly which can be utilized to extrude a catheter tube member formed in accordance with this invention.

Referring now to the drawings, FIG. 1 is a schematic representation of a catheter extruding assemblage, denoted generally by the numeral 2, which can be used to produce the catheter tube portion of the catheter assembly of this invention. The extruding assemblage 2 includes a plurality of resin storage hoppers 4 and 6 that contain the resins that are to be extruded to form the catheter tube. It will be understood that one of the hoppers 2 or 4 contains the stiffest durometer resin component of the catheter tube, and the other of the hoppers contains the softest durometer resin component of the catheter tube. The resins in the hoppers 2 and 4 are preferably the same resin, i.e., polyurethane, PVC, or the like, but the resins in the hoppers 2 and 4 are of different durometers. Preferably, the resin in the higher durometer hopper, say for example hopper 2 will have the durometer of the stiffer proximal end of the catheter tube, and the resin in the lower durometer hopper, which would be hopper 4, will have the durometer of the softer distal end of the catheter tube. A resin extrusion assembly such as that shown in U.S. Pat. No. 4,888,146 granted Dec. 19, 1989 to J. V. Dandeneau can be used to form a catheter tube utilizing the precepts of this invention. The resins are selectively fed through passages 8 and 10 to a mixing chamber 12. Valves 14 and 16 control the respective percentages of the two resins in the mixing chamber 12. The resin mixture is fed from the mixing chamber 12 to an extrusion head 18 from whence the tubular product 20 is extruded. The tubular product has a durometer that varies from one end of the product to the other. The finished product has one end which is soft, with a durometer of about 80 on the Shore A scale, and an opposite end which is harder, with a durometer in the range of about 55 to about 75 on the Shore D scale. The change from the softer durometer to the harder durometer can take place in one or more distinct steps along the length of the product 20, or it can take place gradually along the length of the product 20. The extrusion of the product 20 begins by feeding resin from only one of the hoppers 4 or 6 into the mixing chamber 12 and thence into the extrusion head 18. The emerging end of the product 20 will thus have either the stiffer durometer or the softer durometer, as desired. Once a sufficient length of the initial durometer has been extruded, mixing of the two resins can commence in the mixing chamber 12 so that the durometer of subsequent portions of the product 20 will change. The durometer of the extruded product thus changes from one extreme to the other, back and forth as the extrusion continues. The final catheter tubes are then cut from the extruded product 20 at appropriate locations which will produce the desired result.

FIG. 2 illustrates a catheter component of an embryo implant catheter assembly which is formed in accordance with this invention. The catheter component is denoted generally by the numeral 22, and includes a hollow hub 24 which is secured to a hollow tubular member 26 that is formed from the extruded product 20 described above. The end 28 of the tubular member 26 is termed the "distal end", and the end 30 of the tubular member 30 which is connected to the hub 24 is termed the "proximal end" of the component 22. The distal end 28 of the member 26 is the end which is formed with the softest durometer resin, and the proximal end 30 of the member 26 is the end which is formed from the stiffest durometer resin. FIG. 2 illustrates in phantom lines the manner in which the varying durometer portions of the member 26 affect the flexure of the member 26. There is a proximal portion A of the member which is formed from the stiffer durometer resin which maintains a rectilinear configuration that is coaxial with the hub 24 of the component 22. The portion A is followed by a distal portion B which flexes progressively due to the softer nature of the resin which forms the portion B. The softer portion B includes a distal terminal portion C which is formed from the softest resin, and thus is the most flexible portion of the member 26.

FIG. 3 is an exploded view of the component 22 of FIG. 2 and a guide cannula denoted generally by the numeral 32 which forms a second part of the catheter assembly of this invention. The guide cannula 32 includes a tubular proximal hub 34 and a tubular guide member 36 which is attached to the hub 34.

FIGS. 4 and 5 show how the catheter component 22 and the guide cannula interact during use of the assembly to implant an embryo in a subject's womb. The embryo E to be implanted is seated in the distal end 28 of the member 26 and the catheter component 22 is then inserted into the guide cannula 32. During the step of insertion of the implant assembly into the implant-recipient, the catheter component 22 is retracted into the guide cannula 32 as shown to an extent which causes the guide cannula 32 to shield the embryo E and the distal end 28 of the catheter component 22, as shown in FIG. 4. The proximal portion PP of the member 26 which projects beyond the cannula hub 34 must be formed from the stiffest durometer resin so as to eliminate the likelihood of wobbling of the portion PP of the member 26 when the member 26 is advanced into the guide cannula 32 by the physician during the embryo implant procedure. Wobbling of the remainder of the member 26 during the implant procedure is resisted or prevented by the guide cannula 32. In certain cases, the member 26 may be inserted into the uterus without the use of a guide cannula 32.

FIG. 5 shows the relative positions of the catheter component 22 and the guide cannula 32 at the time the embryo implant is being performed. In order to perform the implant, the catheter component 22 is advanced into the guide cannula 32 after the latter has been inserted to the proper extent into the implant recipient's reproductive organs. Advancement of the catheter component 22 causes a distal portion DP of the member 26 to emerge from the confines of the guide cannula 32 so that the embryo E is advanced further into the recipient past the cannula 32 whereupon the embryo E can be implanted on the uterine wall. The protruding distal portion DP of the member 26 is preferably formed from the softest resin so as to possess the most flexible durometer whereby tissue damage during the implant procedure is minimized. Thus, the proximal portion PP of the catheter member 26 is preferably formed exclusively from a resin having a durometer in the range of about 55 to about 75 Shore D, and the distal portion DP of the catheter member 26 is preferably formed exclusively from a resin having a durometer of about 80 Shore A. The remainder of the catheter member 26, which resides within the guide cannula 32 during the implant procedure, can be formed from resin mixtures which have a durometer which lies between the 55 to about 75 Shore D value to the 80 Shore A value.

FIG. 6 is a cross sectional view of the guide cannula 32 showing details of the construction of the cannula 32. The cannula 32 is preferably formed from a co-extruded composite of an outer resin layer 36 such as polyethylene which possesses memory so that it can be bent in a manner desired by the physician and it will retain the bend. The inner resin layer 38 is formed from a slippery resin such as nylon which facilitates movement of the catheter member 26 through the cannula 32. The cannula 32 can thus be bent to a configuration which allows lateral insertion of the catheter assembly 22 into a body cavity, and also allows the use of a relatively sticky or tacky resin for forming the catheter member 26.

FIG. 7 is a schematic view which illustrates in principal how the assembly of this invention is used to implant an embryo E in the uterus 40 of an implant recipient. The embryo E is placed on the distal tip 28 of the catheter member 26 and the embryo E is then retracted back into the guide cannula 32 so that the embryo E is shielded by the guide cannula 32. The condition of the assembly is thus as shown in FIG. 4. The guide cannula 32 is then advanced into the cervical os 42 until it comes into contact which the cervix 44. The catheter member 26 is then moved forward through the guide cannula 32 so as to push the distal end 28 and the embryo E through the cervix 44 and into the uterus 40. The catheter member 26 is advanced through the uterus 40 until the distal tip 28 of the catheter member 26 contacts the inner uterine wall 46. At this point, a syringe 48 which is connected to the catheter member hub 24 is actuated so as to dislodge the embryo E from the catheter member distal tip 28 and implant the embryo E on the uterine wall 46. It will be appreciated that the soft distal portion DP of the catheter member 26 is sufficiently flexible when extended from the guide cannula 32 to provide a very gentle engagement with the uterine wall 46 so not to damage the latter during the implant procedure. At the same time, the proximal portion PP of the catheter is sufficiently rigid when the guide cannula 32 contacts the cervix 44 to advance the distal end 28 of the catheter 26 through the cervical opening by advancing the catheter hub 24 toward the guide cannula hub 34. By controlling the durometer of the catheter 26 from proximal end to distal end, the desired stiffness is obtained where it is needed and the desired softness is obtained where it is needed. The catheter portions DP and PP should be at least about five centimeters in length for an assembly which is used for human embryo implants.

It will be readily appreciated that an improved catheter assembly will be provided by controlling the durometer of the catheter tube at key locations, which are a predetermined proximal portion of the catheter tube, and a predetermined distal portion of the catheter tube. The improved catheter assembly is obtained without the need to assemble separate catheter tube components, or to structurally reinforce any portions of the catheter tube. The assembly is easy to use by one person and does not require assistance in the final implanting operation of the procedure.

Since many changes and variations of the disclosed embodiment of the invention may be made without departing from the inventive concept, it is not intended to limit the invention except as required by the appended claims.

What is claimed is:

1. An embryo implant catheter assembly comprising a catheter having a soft distal tip end portion for receiving an embryo to be implanted in a female's uterus, and a stiffer proximal end portion for manual manipulation during an embryo implanting procedure, a tubular part of said catheter extending from said proximal end to said distal end of said catheter consisting essentially of a mixture of at least two different extruded resins which have different Shore durometers and wherein the proportions of said resins in said mixture vary from said proximal end to said distal end of said catheter, said tubular part of said catheter being continuous and uninterrupted, and being devoid of seams, joints or internal reinforcing components.

2. The catheter assembly of claim 1 wherein the Shore durometer of said catheter increases gradually from said distal tip end portion to said proximal end portion.

3. The catheter assembly of claim 2 wherein said distal tip end portion of said catheter has a durometer of about 80 shore A, and said proximal end portion of said catheter has a durometer in the range of about 55 to about 75 Shore D.

4. The catheter assembly of claim 3 wherein said catheter includes a medial portion having a durometer which varies between about 80 Shore A to about 55 to about 75 Shore D.

5. The catheter assembly of claim 1 wherein the Shore durometer of said catheter increases stepwise from said distal tip end portion to said proximal end portion.

6. The catheter assembly of claim 5 wherein said distal tip end portion of said catheter has a durometer of about 80 shore A, and said proximal end portion of said catheter has a durometer in the range of about 55 to about 75 Shore D.

7. The catheter assembly of claim 6 wherein said catheter includes a medial portion having a durometer which varies between about 80 Shore A to about 55 to about 75 Shore D.

8. The catheter assembly of claim 1 wherein said catheter distal tip end portion is at least about five centimeters in length.

9. The catheter assembly of claim 8 wherein said catheter proximal end portion is at least about five centimeters in length.

10. The catheter assembly of claim 1 further comprising a guide cannula into which said catheter is inserted, said guide cannula being shorter in length than said catheter whereby said distal end of said catheter can project beyond a distal end of said guide cannula during an embryo implant procedure.

11. The catheter assembly of claim 10 wherein said guide cannula is an extruded resinous member which has an outer resin component that possesses memory and also has an inner slippery resin component that contacts said catheter.

12. The catheter assembly of claim 10 wherein said outer component of said guide cannula is polyethylene and said inner component is nylon.

13. An embryo implant catheter assembly comprising a resinous tubular one-piece undivided catheter having a soft distal tip end portion for receiving an embryo to be implanted in a female's uterus, and a stiffer proximal end portion for manual manipulation during an embryo implanting procedure, said catheter being formed from a mixture of at least two different extruded resins which have different Shore durometers and the stiffness of said catheter at any particular location between said distal and said proximal end portions being determined solely by the Shore Durometer of said mixture at said particular location.

* * * * *